(12) United States Patent
Petersen et al.

(10) Patent No.: US 9,803,664 B2
(45) Date of Patent: Oct. 31, 2017

(54) SYSTEM FOR POSITION MEASURING AND INTEGRITY MEASURING

(71) Applicant: Techni AS, Borre (NO)

(72) Inventors: David Christian Petersen, Åsgårdstrand (NO); Jan Martin Bendiksen, Drammen (NO); Petter F. Schmedling, Moss (NO); Morten Roll Karlsen, Borre (NO); Roland Eisenträger, Sætre (NO); Audun G. Kolle, Horten (NO)

(73) Assignee: TECHNI AS, Borre (NO)

( * ) Notice: Subject to any disclaimer, the term of this patent is extended or adjusted under 35 U.S.C. 154(b) by 173 days.

(21) Appl. No.: 14/397,800

(22) PCT Filed: Apr. 29, 2013

(86) PCT No.: PCT/IB2013/053381
§ 371 (c)(1),
(2) Date: Oct. 29, 2014

(87) PCT Pub. No.: WO2013/164755
PCT Pub. Date: Nov. 7, 2013

(65) Prior Publication Data
US 2015/0085613 A1 Mar. 26, 2015

(30) Foreign Application Priority Data

Apr. 30, 2012 (NO) ................................. 20120504

(51) Int. Cl.
*F15B 15/28* (2006.01)
*F15B 19/00* (2006.01)
(Continued)

(52) U.S. Cl.
CPC .......... *F15B 19/00* (2013.01); *F15B 15/2884* (2013.01); *F15B 19/005* (2013.01); *G01D 5/48* (2013.01); *G01S 15/02* (2013.01)

(58) Field of Classification Search
CPC .................................................... F15B 15/2884
(Continued)

(56) References Cited

U.S. PATENT DOCUMENTS

| 4,126,047 A | 11/1978 | Sethares et al. |
| 5,895,856 A * | 4/1999 | Johnson ............. G01N 29/2412 73/643 |

(Continued)

FOREIGN PATENT DOCUMENTS

| EP | 0 781 994 A2 | 7/1997 |
| EP | 1 323 931 A1 | 7/2003 |

(Continued)

*Primary Examiner* — John Chapman, Jr.
(74) *Attorney, Agent, or Firm* — Birch, Stewart, Kolasch & Birch, LLP (57) ABSTRACT

A system for measuring the position of a rod element as, for example, a hydraulically or pneumatically operated piston rod. Unlike the prior art, the system according to the present invention employs a measuring principle that does not require preparatory treatment of the rod element as is required in the known solutions. The system employs direct time of flight measurements with the aid of acoustic surface waves that are introduced into the rod element. The instrument is retrofittable on existing cylinders without any modification/reconstruction thereof. An EMAT principle is employed to introduce the surface waves into the measurement in a non-contact manner.

11 Claims, 9 Drawing Sheets (51) Int. Cl.
   *G01D 5/48* (2006.01)
   *G01S 15/02* (2006.01)
(58) Field of Classification Search
   USPC .......................................... 73/597, 598, 643
   See application file for complete search history.

(56) References Cited

U.S. PATENT DOCUMENTS

| | | |
|---|---|---|
| 6,119,579 A | 9/2000 | Pawelski |
| 6,318,524 B1 | 11/2001 | Lutz et al. |
| 7,587,930 B2 | 9/2009 | Leclerc et al. |
| 2002/0077734 A1 | 6/2002 | Muller |
| 2007/0214952 A1 | 9/2007 | Kossmann |

FOREIGN PATENT DOCUMENTS

| | | |
|---|---|---|
| FR | 2 867 238 A1 | 9/2005 |
| JP | 2010-237035 A | 10/2010 |
| WO | WO 2010/086582 A2 | 8/2010 |

\* cited by examiner

3 - rod element
100 - a power supply, an arithmetric unit and an operator interface
102 - signal transmitter
103 - signal receiver
106 - distance
111 - EMAT TX unit
112 - EMAT RX unit

Figure 6

3 - rod element
100 - a power supply, an arithmetic unit and an operator interface
102 - signal transmitter
103 - signal receiver
106 - distance
108 - reflector
109 - EMAT TX unit and EMAT RX unit
110 - TX/RX switch

SYSTEM FOR POSITION MEASURING AND INTEGRITY MEASURING

The present invention relates to a system for position measurement, comprising at least one sensor, the system having properties in respect of retrofittability, robustness and accuracy.

The present invention also relates to an assembly where one or more such sensors according to the system are integrated in, for example, linear actuators and mechanical dampers of different kinds. In addition to position measurements, the sensor(s)/system will be capable of being used for integrity monitoring of mechanical elements that are in rotary or translatory motion relative to the sensor(s)/system. By integrity monitoring is meant a technique for, for example, warning of fatigue cracks.

Position measurement is effected in that a measurement of time of flight is made in combination with known parameter(s) from a rod element, for example, the length thereof. The major advantage of the invention is the elimination of the preparatory treatment of the cylinder rod, which gives full retrofittability of such position measuring equipment. To obtain measurement data from the cylinder rod according to this invention, an Electro Magnetic Acoustic Transducer (EMAT) principle is used, whereby the device surrounds the rod element and gives a contact-free transmission of the necessary measuring pulses.

BACKGROUND

In connection with an increasingly more advanced use of linear hydraulic, pneumatic and electric actuators, there has arisen a need for new sensor solutions therefor. In the oil industry there exists a need associated with measurement of the stroke/position of hydraulic cylinders, which cylinders may have stroke lengths in the area of about ten meters and longer. In such hydraulic cylinders, solutions based on gun-drilled holes in piston rods are extremely cost-intensive, and at the same time preclude the replacement of sensors without the whole cylinder being dismantled for renovation. The existing solutions will thus have a number of challenges associated with robustness, accuracy, price and retrofittability.

In connection with regular integrity measurements and monitoring of rotary and translatory elements, there are a number of challenges. One of these challenges is to establish the necessary contact with moving elements in a reliable and long-time stable manner. An example of an application may be continuous monitoring of train axles for, for example, fatigue. Another area may be continuous measurements of shafts in vessels and other similar machine elements that may be subject to reciprocating load with subsequent fatigue cracks and/or other phenomena it is desired to monitor and/or measure in connection with the integrity of machine elements.

An object according to the present invention is therefore to provide a system for position measurement and integrity measurement, wherein one or more disadvantages of the prior art are eliminated or at least minimised.

Another object of the present invention will be to provide a system for position measurement and integrity measurement, where retrofitting on existing cylinders, axles or similar devices is made possible in a simple manner and with a good, producible, robust and long-time stable result.

Yet another object according to the present invention will be to provide a system for position measurement and integrity measurement, where the integrability in the structure of existing products and as a part of existing components is made possible in a simple manner and with a good, producible, robust and long-time stable result.

These objects are achieved by means of a system for position measurement and integrity measurement as disclosed in the following independent claims, with additional features of the invention set forth in the dependent claims and description below.

THE INVENTION

In accordance with a first aspect of the present invention, there is provided a system comprising at least one sensor solution for linear actuators and the like, which system combines robustness, producibility, accuracy and retrofittability at an acceptable cost.

The position measurement and integrity monitoring according to the present invention is provided by means of time of flight measurements in the actual linear translatory and/or rotary object, for example, a cylinder rod. Time of flight measurements as a measuring method for distance measurement is a known principle utilised in a number of products, for example, range finders for surveying. Unlike existing systems based on ultrasonic distance measurement, this invention employs time of flight measurement in the cylinder rod itself. The use of time of flight measurements directly in the cylinder rod material makes it unnecessary to carry out costly preparatory treatment of the cylinder rod as is the case with the Linear Variable Differential Transformer (LVDT) taught, for example, in U.S. Pat. No. 7,587,930 (B2), which is also a technology used for parts of the object of the invention. The scope of the necessary preparatory treatment of the rod element in existing solutions is shown, for example, in WO2010086582 (A2).

In addition to the elimination of the preparatory treatment of the cylinder rod, it is possible to have a retrofittability that is robust without the work that external linear encoders entail.

As compared to solutions based on external meters that employ lasers, radar and the like, the present invention is not dependent on free line of sight between sensor and the point whose position it is desired to find, which may be obstructed by, for example, snow, loose hoses or other obstructing structures or fluids. The present invention is advantageous over other known solutions in that it allows relative translation and rotation between the sensor and the element whose position and/or integrity it is desired to determine.

Measurement of position according to the invention is made possible by acoustic surface waves where the following principle is employed:

An acoustic surface wave with planar wave front is induced in the surface of an acoustic medium, for example, on the cylinder rod of a hydraulic cylinder, and the time is measured from the transmission until the reflection of the pulse from the end(s) of the cylinder rod is received back by the at least one sensor. The speed of sound in the cylinder rod material is known, such that the distance the sound has covered can be calculated. The speed of sound of Rayleigh surface waves in different materials can be determined by calibrations, i.e., by placing TX and RX at a known distance $s_k$ and then measuring the transit time $\tau_k$. The sound of speed in the medium can then be determined from $c=s_k/\tau_k$. When subsequent measurements are made with random distance, it will be possible to determine the distance from $s=c*\tau$.

A reflector can be introduced in the form of a groove milled in the surface perpendicular to the longitudinal direction of the cylinder rod/the direction of travel of the surface wave, or in the form of a collar with a defined edge that is pressed against the cylinder rod. The object is to create a discontinuity in the acoustic impedance that the surface waves meet in order to reflect the waves. The reflector thus follows the movement of the object whose position it is desired to measure. The desired discontinuity in the acoustic impedance also appears in connection with rod seals of various kinds, as is known from typical cylinders and damper structures. The positioning of the sensor fixedly connected to the rod element in one of the following three positions makes possible a number of dynamic continuous position and integrity measurements and/or monitoring:

1. A sensor positioned at the piston face or the closed end of a plunger, positioned with the object of transmitting waves against and receiving them from a discontinuity, for example, provided by or in connection with the cylinder function's sealing function against the cylinder rod or the plunger. Where integrity is concerned, the object is to monitor and/or detect new reflections that arise as a result of changes in the mechanical integrity of the cylinder rod/plunger. Signals to and from a sensor will be provided by means of sliding contacts, flexible conductors or the like.

2. A sensor positioned at the cylinder rod eye or at the end of a plunger that is not in the pressurised medium. The purpose of the positioning is to receive reflections from the acoustic discontinuities that arise from the sealing function against the cylinder housing or is provided solely with the intention of creating such a discontinuity. Where integrity is concerned, the object is to monitor and/or detect new reflections that arise as a result of changes in the mechanical integrity of the cylinder rod/plunger.

3. Positioning the sensor in intermediate positions on the rod element or cylinder housing, motivated by a need for space or special wishes as regards measurement data, is also possible.

4. A positioning of the sensor at the termination of the cylinder housing with the object of transmitting and receiving reflections from discontinuities provided by piston sealing faces, plunger sealing faces or at least a device provided solely for the purpose of producing such a discontinuity, is also possible. Where integrity is concerned, the object is to monitor and/or detect new reflections that arise as a result of changes in the integrity of the cylinder housing.

The system according to the present invention consists of a transmitter and receiver unit, a signal source for the transmitter and also an amplifier, filter and signal conversion into a data signal in the receiver. Overall control of transmitter and receiver as well as signal processing, calculation of distance/position and communication with the surroundings takes place in an attached arithmetic unit.

Another application of the system according to the present invention is that a frequency spectrum is transmitted, and in the response from the rod element its natural frequency is read. Based on known factors such as weight and rigidity, the actual length is calculated.

Time of flight measurements require an interaction between the sensor and the body whose position and/or integrity it is desired to measure. This interaction is, in this invention, intended to be provided by one of the following methods:

1. A transmission principle is employed where the necessary sound is generated in the rod element by means of an Electro Magnetic Acoustic Transducer (EMAT). EMAT is a form of transducer in which a field is used to generate a sound wave in a surface without transducer and surface necessarily coming into contact with one another. In this application, this has a number of advantages as regards wear between parts that move relative to one another. Electromagnetic transduction is a principle for inducing acoustic signals in electrically conductive materials. Here, there are two main principles that have been is use for a long time. One of these principles requires that, in addition to being electrically conductive, the material also is ferromagnetic ($\mu r>1$). This principle makes use of the fact that eddy currents are produced in the material, which then cause mechanical forces that launch the acoustic wave.

2. The second principle on which the invention is based does not require ferromagnetic properties in the material, only that it is electrically conductive, and makes use of so-called Lorentz forces to launch the acoustic wave.

3. A transmission principle is used where ultrasound generated by a piezoelectric element is conducted to and from the rod element by direct contact with the aid of a sliding element of suitable form and material properties, or a rolling element as, for example, a ball or a roller. An elastic element, for example, in the form of a spring, or another pre-tensioning, gives the required contact for transmission of a signal to and from the rod element such that a measurement is possible.

4. The necessary sound wave is generated and detected by a piezoelectric element fixedly connected to the rod element at a suitable point. The electrical connection is established by, for example, sliding contacts, cable or induction principles. Such a solution allows a positioning of the sensor as a part of the cylinder's piston arrangement. A solution of this kind is also conceivably integrated into the termination of the rod element. In situations where a piston arrangement is not used, as is the case when a plunger is used, or the purpose of the sensor is to measure the position of a single rod element in other structures or as an individual element. Fixed positioning of a piezoelectric transducer outside an optionally closed cylinder chamber, for example, by the eye of a hydraulic cylinder, is also a solution in this connection.

A measuring system in accordance with the present invention will advantageously allow, inter alia:

A compact and robust structural form
Low complexity, few parts
No wear parts
Easy retrofittability on existing products
High accuracy
High measuring frequency
Low price

EXAMPLE

In order to give a better understanding of the different technical features and the functions of the present invention a non-limiting exemplary description of an embodiment is given below. The description is given with reference to the drawings, wherein.

Figure 1:
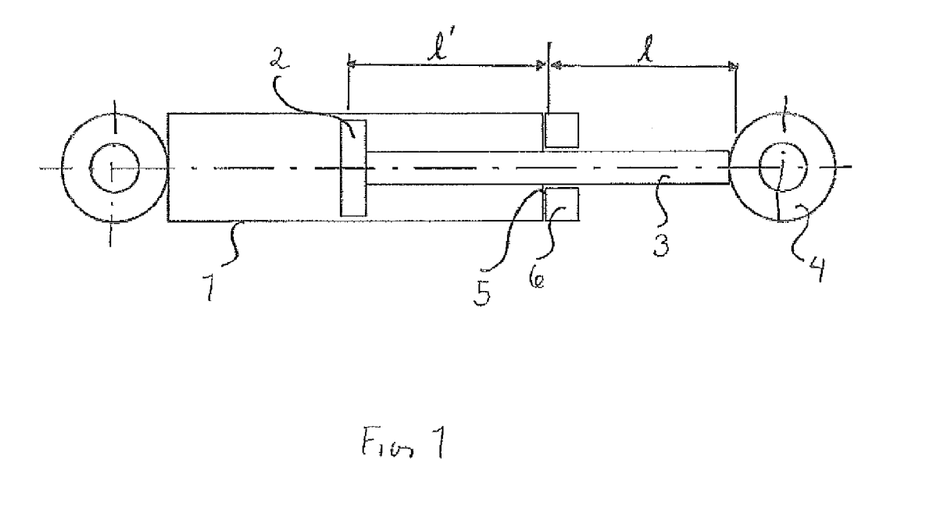
FIG. 1 shows a typical cylinder with which a system according to the present invention can be used.

In FIG. 1 can be seen a typical cylinder 1 in cross-section, the figure indicating a distance (I) between a cylinder seal 5 and an eye 4 mounted at the end of a rod element 3. A distance (I') is also marked and indicates the distance from the seal 5 to the piston element 2 of the cylinder 1. A dividable sensor 6 is mounted around the cylinder rod 3 with the object of providing time of flight measurements in said rod element 3. The sound waves are generated in the sensor 6 and conducted into the rod element 3, where they propagate in the longitudinal direction of the rod element 3. The sound waves spread in both directions, such that they meet the termination of the rod element 3. At one end, the sound waves meet the termination of the rod element 3 where, for example, an eye 4 is mounted. At the other end, the sound waves meet a termination in the form of a transition to a piston element 2. In solutions where a plunger is used, the rod element 3 is terminated without a piston element 2.

The distance to the rod element 3 is calculated in that the speed of sound in the material of the rod element 3 is known. An acoustic surface wave with planar wave front is induced in the surface of the acoustic medium, which acoustic medium in this case is the rod element 3, and the time is measured from the transmission of the acoustic surface wave until the reflection of the pulse from the end/ends of the rod element 3 is received back by the sensor 6. The speed of sound in the material of the rod element 3 is known, such that the distance that the sound has covered can be calculated. The speed of sound of Rayleigh surface waves in different materials can be determined by calibration, i.e., placing TX and RX at a known distance $s_k$ and measuring the transit time $\tau_k$. The speed of sound in the medium can then be determined from the formula $c=s_k/\tau_k$. When subsequent measurements are made with random distance, it will be possible to determine the distance from the formula $s=c\cdot\tau$.

Figure 2:
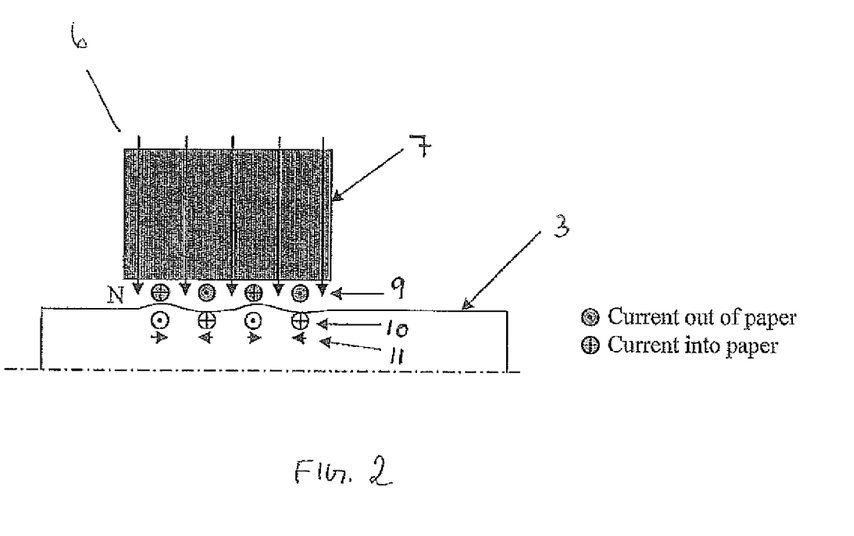
FIG. 2 is a schematic basic diagram of a sensor in the system according to the present invention and a part of a typical cylinder rod.

FIG. 2 shows a schematic basic diagram of the sensor 6 and a part of a typical cylinder rod 3. The sensor 6 comprises a plurality of radially oriented permanent magnets 7 that are mounted in a holder (not shown), the permanent magnets 7 being distributed around the whole or parts of the circumference of the rod element 3. The permanent magnets 7 are so arranged that they have coinciding north/south orientation and surround an antenna 9 in the form of a meander coil 14. Electric current (indicated by vector arrows in and out of the sheet of paper) in the meander coil 14 generates, in interaction with the field from the permanent magnets 7, eddy current 10 (indicated by vector arrows in and out of the paper) with resulting Lorentz forces 11 (indicated by vector arrows in and out of the paper) in the rod element 3, these forces generating an acoustic surface wave that is used in the measurement.

The permanent magnets may, for example, be configured with a toroidal shape and/or an arc-shaped cross-section.

Figure 3:
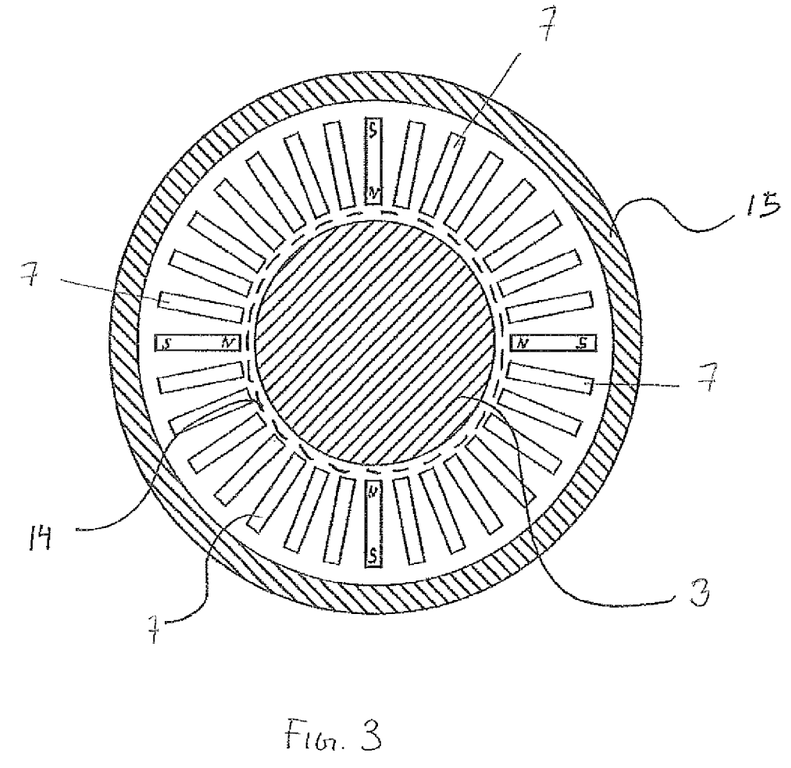
FIG. 3 is a schematic basic diagram of an embodiment of an aspect of radial permanent magnets in the system according to the present invention.

FIG. 3 is a basic diagram showing how the permanent magnets 7 are arranged around the rod element 3. The meander coil 14 is also shown and the whole arrangement is encased in a housing 15 that can be opened in order to encircle the rod element 3.

Figure 4:
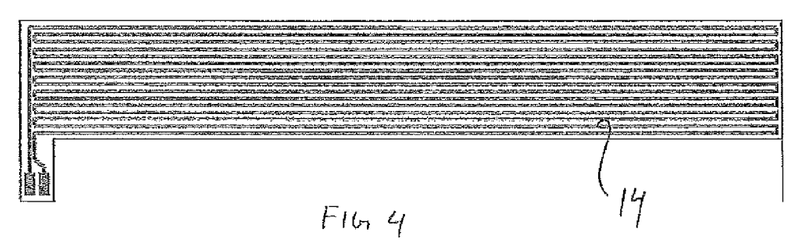
FIG. 4 shows a meander-shaped coil in the system according to the present invention before bending as part of its installation in the sensor.

FIG. 4 shows the meander coil 14 in greater detail, the meander coil 14 being shown in unrolled state, where the meander coil 14 when arranged in the housing 15, will surround the rod element 3 and be arranged within the radial permanent magnets 7.

Figure 5:
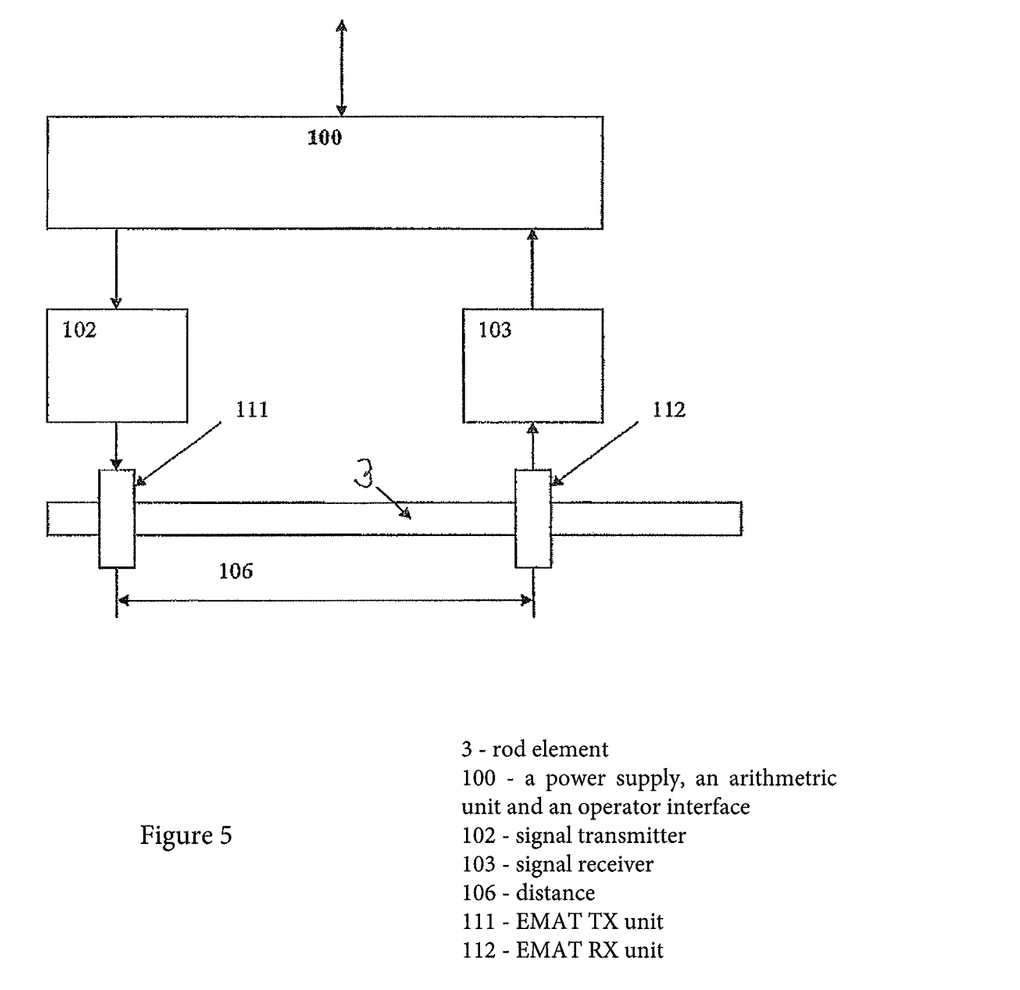
FIG. 5 is a system diagram for a measuring device in the system according to the present invention.

FIG. 5 is a schematic illustration of a measuring device in the system according to the present invention, where a unit 100 comprises a power supply, an arithmetic unit and an operator interface, unit 102 comprises a signal transmitter with associated electronics, unit 103 comprises a signal receiver with associated electronics. The measuring device further comprises an EMAT TX unit 111 and an EMAT RX unit 112. By connecting the different units as shown, a distance 106 in, for example, the rod element 3 can be determined.

The measuring device in the system measures the distance between TX and RX by measuring the time acoustic Rayleigh surface waves take to travel from the TX unit 111 to the RX unit 112. The speed of sound of Rayleigh surface waves in different materials can be determined by calibration, i.e., by placing TX unit 111 and RX unit 112 at a known distance $s_k$ (not shown) and measuring the transit time $\tau_k$. The speed of sound in the medium can then be determined from the formula $c=s_k/\tau_k$. When subsequent measurements are made with random distance $s_k$, it will be possible to determine the distance from the formula $s=c*\tau$.

If the transmitted signal is sufficiently powerful, a receiver in the unit 103 will also receive signals reflected from the two ends of the rod element 3, this allowing position determination of the rod element's 3 ends relative to the transmitter and receiver position.

Figure 6:
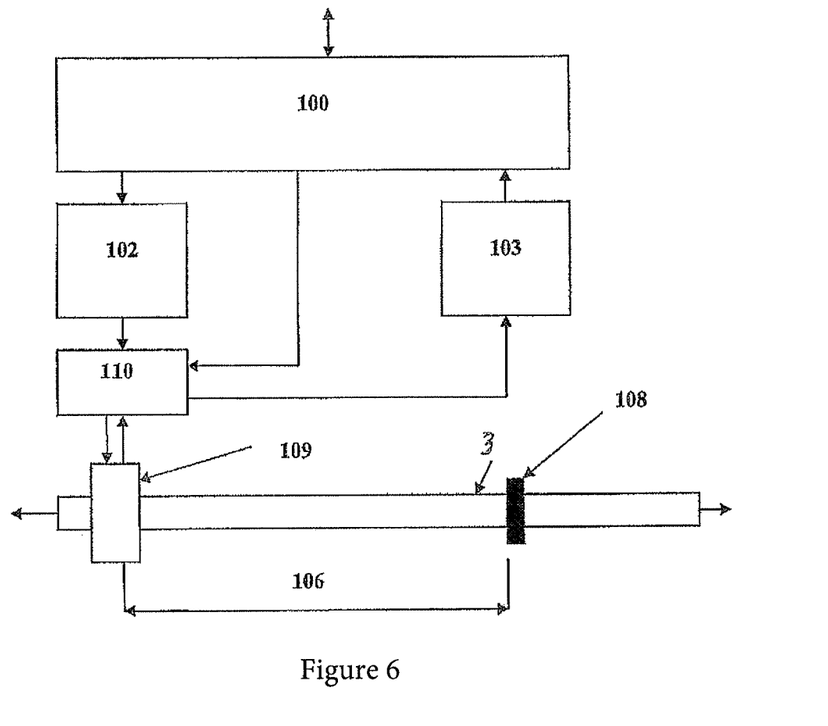
FIG. 6 shows another embodiment of the measuring device shown in FIG. 5.

FIG. 6 is a schematic illustration of another embodiment of a measuring device in the system according to the present invention, where a unit 100 comprises a power supply, an arithmetic unit and an operator interface, a unit 102 comprises a signal transmitter with associated electronics, and a unit 103 comprises a signal receiver with associated electronics. The measuring device further comprises an EMAT TX/RX unit 109 and a reflector 108. By connecting the different units as shown, a distance 106 in, for example, the rod element 3 can be determined. This measuring system is based on the same principles as the measuring device according to FIG. 5, but here the RX and TX antenna will be assembled in one unit 109. In this solution a TX/RX switch 110 is used.

A reflector 108 is introduced in the form of a groove milled in the surface perpendicular to the longitudinal direction of the rod element 3, around the circumference of the rod element 3. Alternatively, a collar (not shown) with a sharp edge can be arranged around the rod element 3, after which the collar is pressed into the surface of the rod element 3. The object is to create a discontinuity in the acoustic impedance that the surface waves meet in order to reflect the wave. The reflector 108 is thus a fixed part of the rod element 3 and will therefore follow the movements thereof.

The distance is now given by the formula $s = c \cdot \tau$.

If the system is regarded as though an EMAT TX/RX is attached to the end of a cylinder from which the piston rod 3 exits, and given that the rod element 3 in FIG. 6 is a piston rod, we will have a system that can determine the position of the piston element 2 (or also the "eye" 4 end of the piston rod 3).

Figure 7:
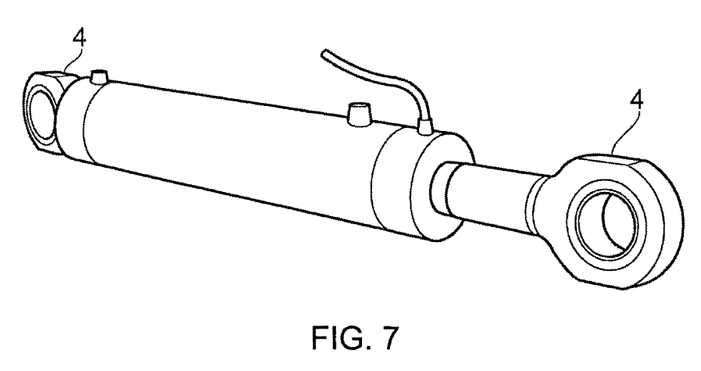
FIG. 7 shows an embodiment of the sensor in the system mounted on a hydraulic cylinder.

FIG. 7 shows a possible embodiment of the system according to the present invention mounted on a typical hydraulic cylinder.

Figure 8:
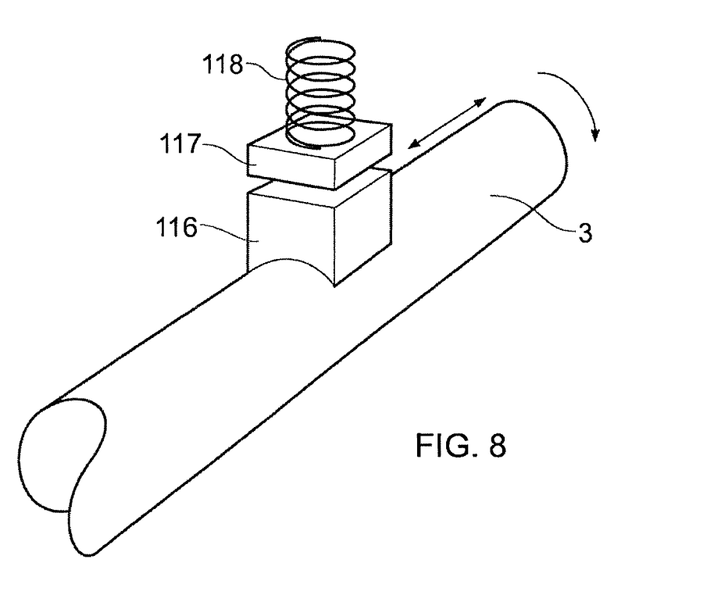
FIG. 8 shows a piezoelectric solution with contact slide.

FIG. 8 shows a sensor arrangement with a slider 116 shaped in conformity with the rod element 3, where a piezoelectric transducer 117 lies pressed against 116 by the spiral spring 118. The spiral spring gives the necessary contact pressure between the part in the arrangement and the rod element 3. The sensor is mounted in a housing (not shown).

Figure 9:
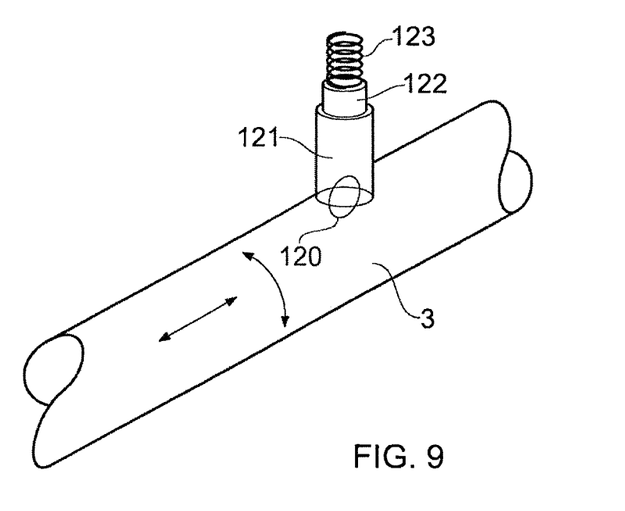
FIG. 9 shows a piezoelectric solution with spherical contact element.

FIG. 9 shows a sensor arrangement where a ball 120 is non-rotationally mounted in a holder 121. A piezoelectric transducer 122 is pressed against the upper edge of the holder 121 by a spiral spring 123. The spiral spring presses the arrangement against the rod element 3. The sensor is mounted in a housing (not shown).

Figure 10:
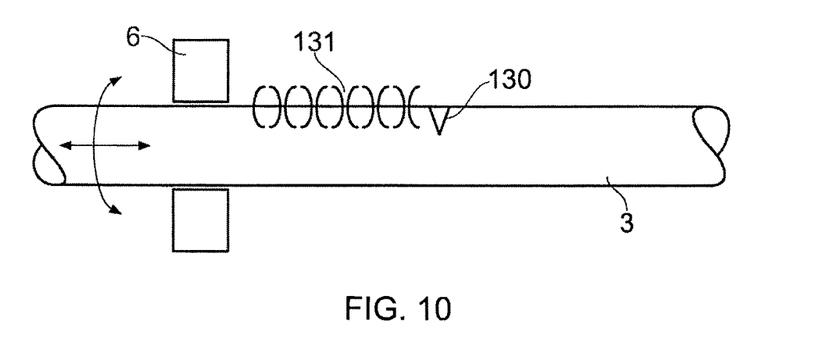
FIG. 10 shows the principle of integrity monitoring by means of the sensor.

FIG. 10 is a schematic illustration of a measuring device for integrity monitoring. The sound waves 131 from the sensor 6 are reflected in the crack 130 as a result of the change in acoustic impedance, which is then registered by the sensor.

The system according to the present invention is, however, not limited to being used in connection with different pneumatic or hydraulic cylinders, but can also be used on different rod elements or the like where position measurement is desirable.

It should be noted that several embodiments are possible. The scope of the invention is limited by the claims, and a person of skill in the art will be able to make numerous changes to the aforementioned examples without departing from the scope of the invention.

The invention claimed is:

1. A system for a pneumatic or hydraulic cylinder, linear guide, damper, or rod element, adapted to provide position measurement by the distance to one and/or both ends of a translatory and/or rotary element,
    wherein an ultrasound-based time of flight measurement is used directly in the translatory and/or rotary element, and that sound waves for the time of flight measurement are generated by a sensor in the form of an EMAT which generates and detects the sound wave, wherein permanent magnets of the sensor are distributed around a circumference of the translatory and/or rotary element and the permanent magnets have a corresponding orientation in the radial direction of the translatory and/or rotary element with respect to their individual north and south orientation.

2. A system according to claim 1, wherein permanent magnets of the sensor are arranged in a torus with an extent covering the whole or parts of a circle surrounding the translatory and/or rotary element in which the sound wave is desired to be introduced and detected.

3. A system according to claim 2, wherein the sensor is mounted onto the pneumatic or hydraulic cylinder, linear guide, damper or rod element without any preparatory treatment of the cylinder body and/or rod elements.

4. A system according to claim 2, wherein the sensor is integrated in a cylinder housing termination.

5. A system according to claim 1, wherein permanent magnets of the sensor are arranged in a torus and have an arc-shaped cross-section with an extent covering the whole or parts of a circle surrounding the translatory and/or rotary element in which the sound wave is desired to be introduced and detected.

6. A system according to claim 5, wherein the sensor is mounted onto the pneumatic or hydraulic cylinder, linear guide, damper or rod element without any preparatory treatment of the cylinder body and/or rod elements.

7. A system according to claim 5, wherein the sensor is integrated in a cylinder housing termination.

8. A system according to claim 1, wherein the sensor is mounted onto the pneumatic or hydraulic cylinder, linear guide, damper or rod element without any preparatory treatment of the pneumatic or hydraulic cylinder, linear guide, damper, or rod element.

9. A system according to claim 8, wherein the sensor is integrated in a cylinder housing termination.

10. A system according to claim 1, wherein the sensor is integrated in a cylinder housing termination.

11. A system for a pneumatic or hydraulic cylinder, linear guide, damper, rod elements, or axles, adapted to provide integrity measurements of a translatory and/or rotary element with the aid of reflections from acoustic impedance changes due to cracks and damage,
    wherein waves for the integrity monitoring are generated by a sensor in the form of an EMAT which generates and detects a sound wave and is fixedly installed, but where the monitored object is able to rotate and/or translate relative to the sensor, wherein permanent magnets of the sensor are distributed around a circumference of the translatory and/or rotary element have a corresponding orientation in the radial direction of the translatory and/or rotary element with respect to their individual north and south orientation.

* * * * *